US007074402B2

(12) United States Patent
Griffin et al.

(10) Patent No.: US 7,074,402 B2
(45) Date of Patent: Jul. 11, 2006

(54) NEUROPROTECTIVE, ANTITHROMBOTIC AND ANTI-INFLAMMATORY USES OF ACTIVATED PROTEIN C (APC)

(75) Inventors: John H. Griffin, Del Mar, CA (US); Berislav Y. Zlokovic, Rochester, NY (US)

(73) Assignee: The Scripps Research Institute, La Lolla, CA (US)

( * ) Notice: Subject to any disclaimer, the term of this patent is extended or adjusted under 35 U.S.C. 154(b) by 132 days.

(21) Appl. No.: 09/777,484

(22) Filed: Feb. 5, 2001

(65) Prior Publication Data

US 2002/0028199 A1    Mar. 7, 2002

Related U.S. Application Data

(60) Provisional application No. 60/180,227, filed on Feb. 4, 2000.

(51) Int. Cl.
*A61K 38/48*    (2006.01)
*A61K 38/36*    (2006.01)
*C07K 14/745*    (2006.01)

(52) U.S. Cl. .............................. 424/94.64; 424/184.1; 514/2; 514/12; 530/381

(58) Field of Classification Search .................... 514/2, 514/8, 12; 424/85.1, 94.64, 198.1; 530/300, 530/350, 351, 399
See application file for complete search history.

(56) References Cited

U.S. PATENT DOCUMENTS

| 5,009,889 | A | * | 4/1991 | Taylor, Jr. et al. ........ 424/94.64 |
| 5,084,274 | A | | 1/1992 | Griffin et al. ............. 424/94.64 |
| 5,254,532 | A | * | 10/1993 | Schwarz et al. ................ 514/2 |
| 6,008,199 | A | * | 12/1999 | Grinnell et al. ................ 514/21 |
| 6,037,322 | A | | 3/2000 | Grinnell et al. ................. 514/8 |
| 6,071,514 | A | * | 6/2000 | Grinnell et al. .......... 424/94.64 |
| 6,268,337 | B1 | * | 7/2001 | Grinnell et al. ................. 514/8 |
| 6,426,071 | B1 | * | 7/2002 | Grinnell et al. .......... 424/94.64 |

FOREIGN PATENT DOCUMENTS

| EP | 0 318 201 A2 | 5/1989 |
| EP | 0 872 245 A1 | 10/1998 |

OTHER PUBLICATIONS

Feigin et al. Recent advances in Huntington's disease: implications for experimental therapeutics. Curr Opin Neurol 15: 483-489, 2002.*
Steece-Collier et al. Etiology of Parkinson's disease's: Genetics and envirnment revisited. Proc Natl Acad Sci USA: 99(22): 13972-13974, 2002.*
Halliday et al. Alzheimer's disease and inflammation: a review of cellular and th rapeutic m chanisms. Clin Exp Pharmacol Physiol 27: 1-8, 2000.*
Cheng et al. Activated protein C blocks p53-mediated apoptosis in ischemic human brain endothelium and is neuroprotective. Nature Med 9(3): 338-342, 2003.*
Arnjlots et al. Antithrombotic effects of activated protein C and protein S in a rabbit model of microarterial thrombosis. Arterioscler Thromb Vasc Biol. 15(7):937-941, 1995.*
Hickenbottom et al. Neuroprotective therapy. Semin Neurol. 18(4):485-492, 1998.*
Yamada et al. Importance of microembolization and inflammation in atheroslerotic heart disease. Am Heart J 140: S90-S102, 2000.*
Li et al. Posttreatment with low molecular weight heparin reduces brain edema and infarct volume in rats subjected to thrombotic middle cerebral artery occlusion. Brain Res. 801(1-2):220-223, 1998.*
Xi et al. Attenuation of thrombin-induced brain edema by cerebral thrombin preconditioning. Stroke. 30(6):1247-1255, 1999.*
Vaughn et al. thrombin receptor activation protects neurons and astrocytes from cell death produced by envoironmental insults. J Neurosci 15(7): 5389-5401, 1995.*
Hirose et al., "Activated protein C reduces the ischemia/ reperfusion-induced sp cord injury in rats by inhibiting neutrophil activation," *Ann Surg* 232(2):272-280 (2000) (eletronic version, pp. 1-10).
Nicolaes et al., "A prothrombinase-based assay for detection of resistance to activated protein C," *Thromb Haemost*, 76(3):404-410 (1996).
Macko, et al., "Brain-Specific Protein C Activation During Cartoid Artery Occlusion in Humans" *Stroke* 30:542-545 (1999).
Shibata, et al., Activated Protein C Protects in a Murine Model of Ischemic Stroke. *Society Neuroscience*, Abstracts -Nov. 2000, 26 (1-2), No. 184.19, see entire abstract.
Shibata, et al., "Anti-Inflammatory, Antithrombotic, and Neuroprotective Effects of Activated Protein C in a Murine Model of Focal Ischemic Stroke" *Circulation* 103:1799-1805 (2001).

* cited by examiner

*Primary Examiner*—Elizabeth Kemmerer
*Assistant Examiner*—Bridget E. Bunner
(74) *Attorney, Agent, or Firm*—DLA Piper Rudnick Gray Cary US LLP

(57) ABSTRACT

The present invention provides methods for treating subjects having or at risk of having a neuropathological disorder or brain inflammatory diseases with and without vascular involvement, and systemic inflammatory vascular disease by administering a therapeutically effective amount of Activated Protein C (APC) to the subject. Brain disorders and brain inflammatory vascular diseases that can be treated by the invention method include all neurodegenerative diseases with different types of neuronal dysfunction, including stroke, Alzheimer's disease, Parkinson's disease, Huntington disease, neuroimmunological disorders such as multiple scelrosis and Gullian-Barre, encephalitis, meningitis, as well as other peripheral vascular diseases, such as diabetes, hypertension, artheriosclerosis. Also included are methods of treatment using APC in combination with a co-factor, such as Protein S.

7 Claims, 8 Drawing Sheets

—○— ischemic   —●— non-ischemic

Control

■ 100%
■ ≥ 50%
▒ < 50%

APC-Treated

□ Control  ■ APC-Treated

NEUROPROTECTIVE, ANTITHROMBOTIC AND ANTI-INFLAMMATORY USES OF ACTIVATED PROTEIN C (APC)

CROSS-REFERENCE TO RELATED APPLICATION

This application claims priority under 35 U.S.C. §119(e)(1) to U.S. provisional application Ser. No. 60/180,227, filed Feb. 4, 2000, which is herein incorporated by reference in its entirety.

ACKNOWLEDGEMENT OF GOVERNMENT INTEREST

This work was supported by NIH Grant No. HL63290. The U.S. Government may have certain rights in this invention.

FIELD OF THE INVENTION

The present invention relates generally to methods for using a new class of neuroprotective agents with additional anticoagulant, anti-inflammatory effects for treatment of pathologies, and more particularly to uses of activated protein C (APC) for the treatment of such pathologies.

BACKGROUND OF THE INVENTION

Serine proteases are a class of proteins that proteolytically cleave other proteins. Members of this class of proteins contribute to important biological processes including the proteolytic cascade reactions of complement activation and blood coagulation. Cleavage of a blood coagulation factor contributes to the coagulation cascade, resulting in blood coagulation. A variety of medical conditions can arise where it is advantageous to inhibit the coagulation cascade at the level of one or another proteolytic step. In addition, procedures involving blood product manipulation can activate members of the cascade, and therefore their specific inhibition is advantageous. The neuroprotective effects of serine-proteases have not been so far recognized.

Protein C (PC) is a member of the class of vitamin K-dependent serine protease coagulation factors. Unlike the majority of coagulation factors, such as Factors VIIa, IXa, Xa, XIIa, thrombin, plasmin or plasma kallikrein which are procoagulants, Protein C regulates blood coagulation by acting as a natural anticoagulant that circulates in the blood in an inactive form that requires proteolytic activation to generate the anticoagulant enzyme. The activated form of Protein C, APC, inhibits blood coagulation at the levels of Factors V and VIII in the clotting cascade.

Similar to most other zymogens of extracellular proteases and the above recited blood coagulation factors, Protein C has the core structure of the chymotrypsin family, having insertions and N-terminus extensions that enable regulation of the zymogen and the enzyme (See Owen W., in *Hemostasis and Thrombosis: Basic Principles and Clinical Practice*, Colman et al., eds, pp. 235–241, J. B. Lippincott Co. (Philadelphia), 1987).

Protein C is composed of domains with discrete structure and function (See Foster et al., *Proc. Natl. Acad. Sci. USA.* 82:4673–4677 (1985) and Plutzky et al., *Proc. Natl. Acad. Sci. USA,* 83:546–550 (1986)). The light chain contains an amino-terminal gamma-carboxyglutamic acid (Gla) region, which is followed by two domains that are homologous to domains in the epidermal growth factor (EGF) precursor. The serine protease activity resides in the heavy chain.

The zymogen is activated by the action of thrombin at the site between the arginine residue at position number 15 of the heavy chain and the leucine residue at position 16 (chymotrypsin numbering) (See Kisiel, *J. Clin. Invest.,* 64:761–769, (1976); Marlar et al., *Blood,* 59:1067–1072 (1982); Fisher et al. *Protein Science,* 3:588–599 (1994)). Other proteins including Factor Xa (Haley et al., *J. Biol. Chem.,* 264:16303–16310 (1989), Russell's viper venom and trypsin (Esmon et al., *J. Biol. Chem.,* 251:2770–2776 (1976) have also been shown to enzymatically cleave and convert inactive protein C to its activated form. Activated protein C (APC) hydrolyzes arginine esters and related substrates via a core triad of catalytic amino acid residues that occur at Ser-195, His-57, and Asp-102 of the heavy chain (chymotrypsin numbering). The enzyme's specificity is restricted to a small number of protein substrates; blood coagulation cofactors, activated Factors V and VIII, as well as Factors V and VIII are the known macromolecular substrates for the proteolytic inactivation by activated protein C (See Kisiel et al., *Biochem.,* 16:5824–5831 (1977); Vehar et al., *Biochem.,* 19:401–410 (1980); and Walker et al., *Biochim. Biophys. Acta.,* 571:333–342 (1979)).

Thrombin, thought to be the major physiological protein C activator, activates protein C slowly in purified systems, plasma, or blood, when in the presence of physiological concentrations of calcium. A membrane-bound thrombin receptor called thrombomodulin has been identified which accelerates protein C activation. Thrombin binds to thrombomodulin on the luminal surface of endothelial cells and undergoes an increase in specificity for protein C. Calcium is required for this process. Additional studies have revealed that the membrane-lipid binding domain of protein C, the vitamin-K dependent Gla domain, is also required for normal activation of protein C (Esmon et al., in "Progress in Vascular Biology, Hemostasis, and Thrombosis", Ruggeri et al., eds., *Annals of The New York Academy of Sciences,* Vol. 614:30–43 (1991)). Endothelial protein C receptor (EPCR) enhances protein C activation by thrombin bound to thrombomodulin.

Thrombosis and thromboembolism, the occurrence of occlusive thrombi in the vasculature of human patients, poses a significant clinical problem and is a significant cause of morbidity and mortality. Arterial thrombi are responsible for myocardial infarction (MI) and cerebral ischemia (stroke), while venous thrombi cause deep vein thrombosis (DVT) and pulmonary embolism (PE). The magnitude of the clinical challenge created by thrombi is reflected in morbidity and mortality statistics. One of the leading causes of death in men over the age of 50 is acute MI, and stroke remains a debilitating and unpredictable disease.

Deep vein thrombosis is a common disease. Well established risk factors include recent surgery, malignant disorders, pregnancy and labor, long term immobilization, and deficiency of one of the main inhibitors of the clotting system. The main inhibitors are known to be protein C, protein S and antithrombin. The causes of deep vein thrombosis in many patients remain unclear. It has recently been established however that a poor anticoagulant response to activated protein C (APC) is present in many families with a hereditary tendency to venous thrombosis.

Inflammation is the body's reaction to injury and infection. Three major events are involved in inflammation: (1) increased blood supply to the injured or infected area; (2) increased capillary permeability enabled by retraction of endothelial cells; and (3) migration of leukocytes out of the capillaries and into the surrounding tissue (hereinafter referred to as cellular infiltration) (Roitt et al., *Immunology*, 1 Grower Medical Publishing, New York, 1989)).

Increased capillary permeability allows larger molecules to cross the endothelium that are not ordinarily capable of doing so, thereby allowing mediators of immunity such as leukocytes to reach the injured or infected site. Leukocytes, primarily neutrophil polymorphs (also known as polymorphonuclear leukocytes, neutrophils or PMN) and macrophages, migrate to the injured site by a process known as chemotaxis. At the site of inflammation, tissue damage and complement activation cause the release of chemotactic peptides, such as C5a. Complement activation products are also responsible for causing degranulation of phagocytic cells, mast cells and basophils, smooth muscle contraction and increases in vascular permeability (Mulligan et al. *J. Immunol.* 148:1479–1485 (1991)).

Although leukocyte traversal of vessel walls to extravascular tissue is necessary for host defense against foreign antigens and organisms, leukocyte-endothelial interactions often have deleterious consequences for the host. For example, during the process of adherence and transendothelial migration, leukocytes release oxidants, proteases and cytokines that directly damage endothelium or cause endothelial dysfunction. Once at the extravascular site, emigrated leukocytes further contribute to tissue damage by releasing a variety of inflammatory mediators. Moreover, single leukocytes sticking within the capillary lumen or aggregation of leukocytes within larger vessels are responsible for microvascular occlusion and ischemia. Leukocyte-mediated vascular and tissue injury has been implicated in pathogenesis of a wide variety of clinical disorders, such as acute and chronic allograft rejection, vasculitis, rheumatoid and other forms of inflammatory based arthritis, inflammatory skin diseases, adult respiratory distress syndrome, ischemia-reperfusion syndromes such as myocardial infarction, shock, stroke, organ transplantation, crush injury and limb replantation.

Many other serious clinical conditions involve underlying inflammatory processes in humans. For example, multiple sclerosis (MS) is an inflammatory disease of the central nervous system. In MS, circulating leukocytes infiltrate inflamed brain endothelium and damage myelin, with resultant impaired nerve conduction and paralysis (Yednock et al., *Nature* 366:63–66 (1992)). Systemic lupus erythematosus (SLE) is an autoimmune disease characterized by the presence of tissue damage caused by self antigen directed antibodies. Auto-antibodies bound to antigens in various organs lead to complement-mediated and inflammatory cell mediated tissue damage (Theofilopoubs, A. N., *Encyclopedia of Immunology*, pp. 1414–1417 (1992)).

Reperfusion injury is another condition associated with activation of the inflammatory system and enhanced leukocyte-endothelial cell (EC) adhesion. There is much evidence that adhesion-promoting molecules facilitate interactions between leukocytes and endothelial cells and play important roles in acute inflammatory reaction and accompanying tissue injury. For example, in acute lung injury caused by deposition of IgG immune complexes or after bolus i.v. infusion of cobra venom factor (CVF), neutrophil activation and the generation of toxic oxygen metabolites cause acute injury (Mulligan et al., *J. Immunol.* 150(6):2401–2405 (1992)). Neutrophils (PMNs) are also known to mediate ischemia/reperfusion injury in skeletal and cardiac muscle, kidney and other tissues (Pemberton et al., *J. Immunol.* 150:5104–5113 (1993)).

Infiltration of airways by inflammatory cells, particularly eosinophils, neutrophils and T lymphocytes, is a characteristic feature of atopic or allergic asthma (Cotran et al., *Pathological Basis of Disease*, W. B. Saunders, Philadelphia, 1994). Cellular infiltration of the pancreas with resultant destruction of islet beta-cells is the underlying pathogenesis associated with insulin-dependent diabetes melitis (Burkly et al., *Diabetes* 43: 529–534 (1994)). Activation of inflammatory cells whose products cause tissue injury underlies the pathology of inflammatory bowel diseases, such as Crohn's disease and ulcerative colitis (Cotran et al., 1994). Neutrophils, eosinophils, mast cells, lymphocytes and macrophages contribute to the inflammatory response. Minute microabcesses of neutrophils in the upper epithelial layers of the dermis accompany the characteristic epidermal hyperplasia/thickening and scaling in psoriasis.

Various anti-inflammatory drugs are currently available for use in treating conditions involving underlying inflammatory processes. Their effectiveness however, is widely variable and there remains a significant clinical unmet need. This is especially true in the aforementioned diseases where available therapy is either of limited effectiveness or is accompanied by unwanted side effect profiles. Moreover, few clinical agents are available which directly inhibit cellular infiltration, a major underlying cause of tissue damage associated with inflammation. Thus, there is a need for a safe, effective clinical agent for preventing and ameliorating cellular infiltration and consequential pathologic conditions associated with inflammatory diseases, injuries and resultant perturbations of cytokine networks.

Therefore, there is a need in the art for new and better compounds and methods of their use in treating diseases associated with inflammation, thrombosis, and a variety of types of neurological damage.

SUMMARY OF THE INVENTION

The present invention overcomes many of these problems in the art by providing, in a first embodiment, methods for reducing inflammation in a subject having or at risk of having inflammatory vascular disease. The method includes administering to the subject, an anti-inflammatory effective amount of activated protein C (APC), thereby reducing inflammation in the subject.

In another embodiment, the invention provides methods for protecting neuronal cells from cell death in a subject having or at risk of having a neuropathological disorder by administering to the subject a neuroprotective effective amount of activated protein C (APC), thereby providing neuroprotection to the subject.

In yet another embodiment, the invention provides a method for reducing inflammation in a subject having or at risk of having a neuropathological disorder. The method includes administering to the subject, an anti-inflammatory effective amount of activated protein C (APC), thereby reducing neurological inflammation in the subject.

BRIEF DESCRIPTION OF THE FIGURES

FIG. 2A shows the volumes of brain infarction (left) and edema (Swanson correction, right). Values are mean±SE, n=6 for control mice, and n=7 for APC-treated mice. *p<0.01 and **p<0.05 by Student's t-test. FIG. 2B shows the infarct area for each of the five coronal sections of the same brain as in FIG. 2A. Values are mean±SE; *p<0.05.

FIG. 5A shows signal from Western blot standard curve samples was linear in the range between 0.05 and 3 µg/0.1 ml. FIG. 5B shows Western blot analysis of 10 mg brain tissue sections at the level of the optic chiasma in control and APC-treated mice in the ischemic and contralateral hemispheres. Fibrin levels were determined by scanning densitometry using the standard curve (mean±SE, n=3).

DETAILED DESCRIPTION OF THE INVENTION

Figure 1A:
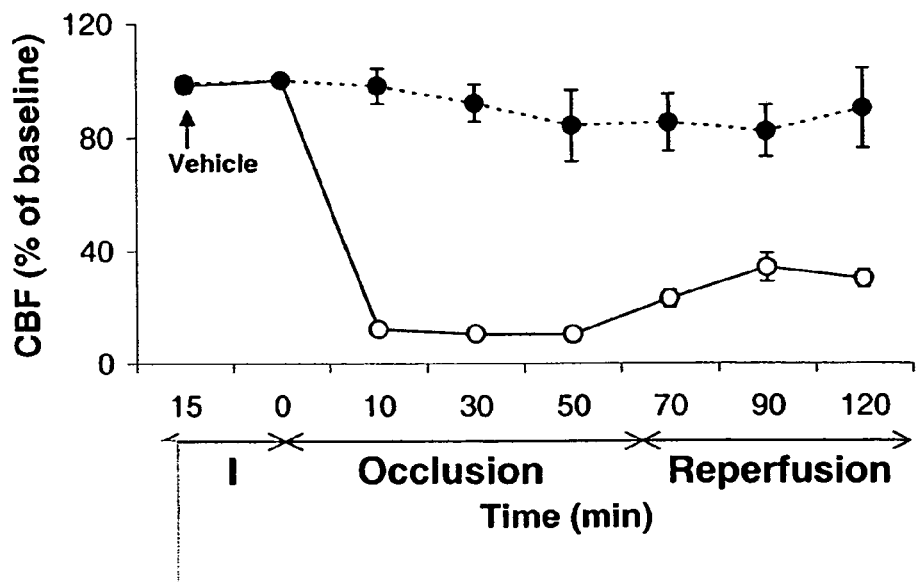
FIGS. 1A and 1B are graphs showing changes in cerebral blood flow (CBF) during MCA occlusion and reperfusion in control mice (FIG. 1A) and APC-treated mice (FIG. 1B). Time period (I) corresponds to CBF values taken after IV administration of either vehicle (FIG. 1A) or APC (FIG. 1B) prior to occlusion. Values are expressed as mean±SD, n=6 for control group and n=7 for APC-treated group. Significant differences in CBF values between the two groups are indicated by a star (*) (p<0.02 to <0.005).

The present invention is based on the seminal discovery that APC has significant—neuroprotective, antithrombotic and anti-inflammatory effects of APC in a murine model of transient focal cerebral ischemia with cerebrovascular thrombosis whether administered before or after the ischemic event. In this model, reductions in the cerebral blood flow (CBF) during middle cerebral artery (MCA) occlusion and reperfusion in control animals were more pronounced than in previously reported murine stroke models, i.e., by about 2 to 3-fold, respectively, leading to large brain infarcts, swelling, development of significant inflammatory response, thrombosis and death relatively early during reperfusion. Treatment with APC either before or after induction of stroke protected mice from accelerated stroke-related death and restored CBF almost completely during MCA reperfusion. These effects were associated with significant reductions in the extent of brain injury and swelling, and improvement in motor neurological performance. While not wanting to be bound to a particular theory, it is believed that the neuroprotective effects of APC are related to its anti-inflammatory activities, as suggested by the remarkable reduction in number of PMNs that infiltrate the ischemic hemisphere (due to prevention of their migration across the blood-brain barrier), and also due to its antithrombotic effects, as suggested by the significant reduction in cerebrovascular fibrin deposits in stroke-induced animals.

The beneficial effects of APC in the present invention were associated with marked improvement of post-ischemic re-circulation, i.e., 79% of baseline CBF values in comparison to only 32% in control animals. It is possible that the observed CBF improvement involves, in part, alleviation of post-ischemic coagulopathy by APC. Previous studies of global ischemia revealed massive intravascular coagulation in association with complement activation. Studies in focal ischemia models also revealed that significant obstructions in CBF might result from massive microvascular occlusions due to vascular accumulation of polymorphonuclear (PMNs) leukocytes and fibrin deposition. Animals which lack a key fibrinolytic factor, for example tPA−/− mice, may develop substantial ischemic brain thrombosis and injury even when the CBF was only moderately reduced. While previous studies involving organs other than brain reported significant anticoagulant activity of APC in vitro and in vivo in different microarterial thrombosis models, the present study demonstrates not only anticoagulant effects but also anti-inflammatory and neuroprotective effects of APC.

Given the data provided in the Examples described herein, it is believed that anti-inflammatory effects of APC contribute to restoration of post-ischemic CBF. The Examples show that APC, in addition to significantly reducing fibrin deposition in the ischemic hemisphere, also prevents intravascular accumulation of peripheral blood cells, i.e., PMNs, in brain by preventing their transport across the blood-brain barrier. Although the mechanisms of anti-inflammatory effects of APC are still not completely understood, the absence of significant leukocyte-endothelial interactions in ischemic APC-treated animals may not only reduce fibrin formation in ischemic brain, but could also be related to improvements in the CBF and reduced neuronal injury. It has been shown that blocking PMN penetration across the blood-brain barrier results in considerable improvement of the neurological outcome and also limits neuronal injury.

The inventors now believe that one of the mechanisms by which APC minimizes damage in both the cerebral vascular system and brain is by reducing inflammatory reactions. The present study demonstrated that APC prevented stroke-related death, reduced volumes of brain infarction and edema by 59% and 50%, respectively, and improved motor neurologic score by 2-fold. It is likely that the increased velocity of post-ischemic re-circulation results in faster restoration of energy-producing metabolites, recovery of the redox state of the respiratory chain and restoration of normal tissue energy state with reactivation of ion exchange pumps, which are pivotal for normal neuronal functioning and elimination of post-ischemic edema. The capability of APC to abolish almost completely leukocyte accumulation within the vascular system and prevent PMN penetration into brain parenchyma may be responsible, in part, for its neuroprotective effects. This may increase not only the rate of re-circulation, but may also importantly alleviate post-ischemic generation of reactive oxygen species from PMNs, which in turn may protect neurons from injury. Although the neuroprotective effects of APC in stroke can be rationalized by its anti-inflammatory action and antithrombotic effects, we cannot rule out the possibility that APC itself may also have direct neuroprotective effects on neurons.

The present study indicated that APC does not adversely affect hemostatic function or produce increased bleeding in the brain or intracerebral hemorrhage (ICH). This confirms findings from previous experimental studies with APC in demonstrating that elevated levels of APC appear not to cause bleeding. In contrast to APC, bleeding and ICH were reported as potential life-threatening complications with other forms of antithrombotic therapy for stroke including thrombolytic treatment with plasminogen activators (e.g., tPA) or anticoagulant treatment with heparin.

Prospective epidemiological studies have suggested that endogenous protein C zymogen may be protective in stroke in humans. Low levels of plasma protein C or APC, and/or resistance to the anticoagulant effects of APC were related to poor outcome after stroke. Low plasma levels of protein C observed in stroke patients may be caused by lower levels of protein C biosynthesis and/or by protein C depletion due to excessive thrombin generation and rapid APC clearance, while low circulating APC may result from depletion of protein C zymogen precursor, increased levels of circulating APC inhibitors, or reduced APC generating capacity due to either low levels of intravascular thrombin, or reduced thrombomodulin and/or endothelial cell protein C receptor. It has been speculated that generation of APC from ischemic tissues is protective, for example during cerebral ischemia in humans and after cardiopulmonary bypass surgery. Results presented here give insights into previous clinical studies and suggest the potential relevance of APC as a neuroprotective agent with multiple actions that may be beneficial for clinical applications in stroke.

Neurodegenerative diseases include diseases in which neuronal cells degenerate to bring about a deterioration of cognitive functions. A variety of diseases and neurological deficiencies may bring about the degeneration of neuronal cells, including Alzheimer's disease, Huntington disease or chorea, hypoxia or ischemia caused by stroke, cell death caused by epilepsy, amyotrophic lateral sclerosis, mental retardation and the like, as well as neurodegenerative changes resulting from aging.

In a first embodiment, the invention provides methods for reducing inflammation in a subject having or at risk of having inflammatory vascular disease. The method includes administering to the subject, an anti-inflammatory effective amount of activated protein C (APC), for example, in a pharmaceutically acceptable carrier, thereby reducing inflammation in the subject.

The present invention is useful for treating many clinical conditions involving inflammatory processes. For example, inflammatory bowel diseases including Crohn's disease and ulcerative colitis are spontaneous chronic inflammations of the gastrointestinal tract which involve activation of inflammatory cells whose products cause tissue injury. Neutrophils, eosinophils, mast cells, lymphocytes and macrophages contribute to the inflammatory response. While not wanting to be bound to a particular theory, it is speculated that APC acts on brain endothelial cells (i.e., vascular cells), via an endothelial receptor for protein C and APC, that mediates its effects on endothelium, both central and peripheral. This, in turns affects intracellular signaling systems that in a cascade turn on and off different genes in vascular endothelium that may interfere with normal endothelial cell response to inflammation. For example, it is known that adhesion molecules mediate the interactions of leucocytes with the vessel wall. It is possible that APC prevents their expression and this is why the inflammatory response is inhibited. Adhesion molecules that may mediate this response may include molecules such as ICAM, VCAM, or PECAM.

The present invention is also directed to treatment of systemic shock and many resultant clinical conditions associated therewith. Systemic shock often occurs as a complication of severe blood loss, severe localized bacterial infection and ischemia/reperfusion trauma and it is a major cause of death in intensive care units. Most cases of septic shock are induced by endotoxins (i.e., bacterial cell wall lipopolysaccharides or LPS) from gram negative bacilli or toxins (i.e., toxic shock toxin 1) from gram positive cocci bacteria. The release of LPS in the bloodstream causes release of inflammatory mediators (inflammatory cytokines, platelet activating factor, complement, leukotrienes, oxygen metabolites, and the like) which cause myocardial dysfunction, vasodilation, hypotension, endothelial injury, leukocyte adhesion and aggregation, disseminated intravascular coagulation, adult respiratory distress syndrome (ARDS), liver, kidney and central nervous system (CNS) failure. Shock due to blood loss also involves inflammatory mediator release. In each case, inflammatory responses are induced at the original site of trauma, and also in the vasculature and remote vascularized sites.

Myocardial ischemia is associated with activation of the complement system which further promotes cardiac injury with the enhancement of a series of inflammatory events. Life threatening local and remote tissue damage occurs during surgery, trauma and stroke when major vascular beds are deprived for a time of oxygenation (ischemia), then restored with normal circulation (reperfusion). Reperfusion injury is characterized by vascular permeability leading to edema and infiltration of inflammatory cells. Neutrophils contribute significantly to reperfusion damage by generating oxidants or releasing proteases that damage the microvasculature or adjacent tissue. Cell death and tissue damage due to complement and inflammatory cell mechanisms lead to organ failure or decreased organ function. The activation of mediators by a local injury can also cause a remote injury to highly vascularized organs. The compositions and methodologies of the present invention are useful in the treatment of ischemia and reperfusion injury.

Inflammatory response damage also occurs in glomerulonephritis as well as tubule disease. Infiltration of inflammatory cells (especially macrophages) is linked to proteinuria accompanied histologically by hypercellularity and crescent formation in glomeruli. Over a longer term, the infiltration of inflammatory cells is associated with accumulation of extracellular matrix and sclerosis and chronic compromise of renal function. The present invention is also efficacious in treating glomerulonephritis and tubule disease.

There are many other disease and injury conditions which benefit from the methodologies of the present invention such as for example, coronary arterial occlusion, cardiac arrhythmias, congestive heart failure, cardiomyopathy, bronchitis, acute allergic reactions and hypersensitivity, neurotrauma, graft/transplant rejection, myocarditis, insulin dependent diabetes, and stroke. Stroke involves a very strong inflammatory response, that in part may be responsible for neuronal damage directly by allowing leukocytes to enter the brain and destroy normal brain cells and neurons, and indirectly by obstructing microvessels and stopping blood flow. This again requires adhesion molecules and cytokines that may be direct or indirect targets of APC cellular interactions that are independent of its anticoagulant effects.

In addition to treating patients suffering from the trauma resulting from heart attack, patients suffering from actual physical trauma could be treated with APC in order to relieve the amount of inflammation and swelling which normally result after an area of the body is subjected to severe trauma. Also, patients suffering from hemorrhagic shock could be treated to alleviate inflammation associated with restoring blood flow. Other disease states which might be treatable using formulations of the invention include various types of arthritis, various chronic inflammatory conditions of the skin, insulin-dependent diabetes, and adult respiratory distress syndrome. After reading the present disclosure, those skilled in the art will recognize other disease states and/or symptoms which might be treated and/or mitigated by the administration of APC formulations of the present invention.

Some examples of arterial thrombosis where APC alone or in combination with a thrombolytic agent, anticoagulant, or anti-inflammatory is useful include the following clinical settings: 1) Acute arterial thrombotic occlusion including coronary, cerebral or peripheral arteries; 2) Acute thrombotic occlusion or restenosis after angioplasty; 3) Reocclusion or restenosis after thrombolytic therapy. Thrombolytic agents such as t-PA salvage ischemic tissue when used within hours of acute heart attack or stroke by re-establishing blood flow in the occluded artery. At present, between one-fourth and one-third of patients who have successful thrombolytic reperfusion of occluded coronary arteries subsequently undergo reocclusion after discontinuing t-PA infusion. This complication occurs despite full-dose heparin therapy. APC will have greater efficacy than heparin in preventing reocclusion. 4) Small and large caliber vascular graft occlusion. Vascular grafts of small caliber, i.e., 3-/mm diameter, have a high frequency of thrombotic occlusion. APC alone or in combination with a thrombolytic agent is useful to prevent occlusion. 5) Hemodialysis. The prosthetic surfaces and flow design of all hemodialyzers are thrombogenic. Currently heparin is infused during dialysis. However, heparin is only partially effective, thereby limiting the reuse of dialyzers. Also, heparin has a number of troublesome side effects and complications. 6) Cardiopulmonary bypass surgery. To prevent thrombus formation in the oxygenator and pump apparatus, heparin is currently used. However, it fails to inhibit platelet activation and the resultant transient platelet dysfunction which predisposes to bleeding problems post-operatively. 7) Left ventricular cardiac assist device. This prosthetic pump is highly thrombogenic and results in life threatening thromboembolic events—complications that are only partially reduced by conventional anticoagulants (heparin or coumarin drugs). 8) Total artificial heart and left ventricular assist devices. 9) Other arterial thrombosis. APC is useful for arterial thrombosis or thromboembolism where current therapeutic measures are either contraindicated or not effective. For example, APC is useful for the treatment of acute pre- or postcapillary occlusion, including transplantations, retina thrombosis, or microthrombotic necrosis of any organ complicating infections, tumors, or coumarin treatment.

In another embodiment, the present invention provides methods for protecting neuronal cells from cell death in a subject having or at risk of having a neuropathological disorder is provided. The method includes administering to the subject, a neuroprotective effective amount of activated protein C (APC), for example, in a pharmaceutically acceptable carrier, thereby providing neuroprotection to the subject. Examples of "neuropathological disorders" include but are not limited to stroke, Alzheimer's disease, Huntington disease, ischemia, epilepsy, amyotrophic lateral sclerosis, mental retardation and aging. One "having or at risk of having" an inflammatory vascular disease as described herein is a subject either exhibiting symptoms of the disease or diagnosed as being at risk for developing the disease. Such subjects include those subjects having undergone or preparing for surgical procedures as described below.

In yet another embodiment, the invention provides methods for reducing inflammation in a subject having or at risk of having a neuropathological disorder. The method includes administering to the subject, an anti-inflammatory effective amount of activated protein C (APC), for example in a pharmaceutically acceptable carrier, thereby reducing neurological inflammation in the subject. The methodologies of the present invention are also efficacious in the treatment of multiple sclerosis (MS) in addition to the neuropathologies described above. MS is often characterized by the penetration of the blood-brain barrier by circulating leukocytes, leading to demyelination in various parts of the brain, impaired nerve conduction and, ultimately, paralysis.

The term "treatment" or "ameliorate" refers to reducing the symptoms of the disease, such as inflammation. The term "treatment" or "ameliorate" denotes a lessening of the detrimental effect of the inflammatory or neurological disease in the subject receiving therapy. The term "treatment" when referring to neurological disease used hereinafter does not necessarily mean that the neurodegenerative disease is completely eliminated, but rather that the cognitive facilities damaged by the disease are improved. "Therapeutically effective" as used herein, refers to that amount of APC that is of sufficient quantity to ameliorate the cause or symptoms of the disease. The subject of the invention is preferably a human, however, it can be envisioned that any animal in need of anti-inflammatory or neuroprotection can be treated using the methods of the invention.

The term "neurodegenerative disease" is used hereinafter to denote conditions which result in degeneration of neural cells in the brain which may bring about deterioration of cognitive function. Such degeneration of neural cells may be caused by Alzheimer's disease (e.g., Alzheimer's disease is characterized by synaptic loss and loss of neurons) Huntington disease or chorea; by pathological conditions caused by temporary lack of blood or oxygen supply to the brain, e.g., brought about by stroke; by epileptic seizures; due to chronic conditions such as amyotrophic lateral sclerosis, mental retardation; as well as due to normal degeneration due to aging. It should be noted that diseases such as stroke and Alzheimer's have both a neurodegenerative and an inflammatory vascular component and thus are treatable by the methods of the invention.

One aspect of the invention includes the "neuroprotective" activity of APC. The term "neuron" includes hundreds of different types of neurons, each with distinct properties. Each type of neuron produces and responds to different combinations of neurotransmitters and neurotrophic factors.

Neurons are thought not to divide in the adult brain, nor do they generally survive long in vitro. The method of the invention provides for the protection from death or senescence of neurons from virtually any region of the brain and spinal cord. Neurons include those in embryonic, fetal or adult neural tissue, including tissue from the hippocampus, cerebellum, spinal cord, cortex (e.g., motor or somatosensory cortex), striatum, basal forebrain (cholenergic neurons), ventral mesencephalon (cells of the substantia nigra), and the locus ceruleus (neuroadrenaline cells of the central nervous system).

Whether in the brain or other tissue, APC acts on brain endothelial cells (i.e., vascular cells), via endothelial receptor(s) for protein C and APC, that mediates its effects on endothelium, both central and peripheral. This in turn affects intracellular signaling systems that in a cascade turn on and off different genes in vascular endothelium that may interfere with normal endothelial cell response to inflammation. It is also possible that receptors for APC on neurons may mediate neuroprotective effects of APC.

Thus, in one aspect of the invention, it may be desirable to up-regulate the expression of such receptors in order to more effectively treat a particular disease.

The present invention is useful for treating many clinical conditions involving inflammatory processes. For example, inflammatory bowel diseases including Crohn's disease and ulcerative colitis are spontaneous chronic inflammations of the gastrointestinal tract which involve activation of inflammatory cells whose products cause tissue injury. Neutrophils, eosinophils, mast cells, lymphocytes and macrophages contribute to the inflammatory response.

In addition to administering APC to a subject as described herein, it may be desirable to co-administer one or more anti-inflammatory agent or additional neuroprotective agent. Co-administration may include administration prior to APC, simultaneously with APC or following APC administration.

Non-limiting examples of neuroprotective agents include N-methyl-D-aspartate (NMDA) receptor antogonists and calcium ion channel antagonists, such as are known in the art, and the like.

Examples of anti-inflammatory agents include but are not limited to: Aminoarylcarboxylic Acid Derivatives such as Etofenamate, Meclofenamic Acid, Mefanamic Acid, Niflumic Acid, Arylacetic Acid Derivatives such as Acemetacin, Amfenac, Cinmetacin, Clopirac, Diclofenac, Fenclofenac, Fenclorac, Fenclozic Acid, Fentiazac, Glucametacin, Isoxepac, Lonazolac, Metiazinic Acid, Oxametacine, Proglumetacin, Sulindac, Tiaramide, Tolmetin, Arylbutyric Acid Derivatives such as Butibufen, Fenbufen, Arylcarboxylic Acids such as Clidanac, Ketorolac, Tinoridine, Arylpropionic Acid Derivatives such as Bucloxic Acid, Carprofen, Fenoprofen, Flunoxaprofen, Ibuprofen, Ibuproxam, Oxaprozin, Piketoprofen, Pirprofen, Pranoprofen, Protizinic Acid, Tiaprofenic Acid, Pyrazoles such as Mepirizole, Pyrazolones such as Clofezone, Feprazone, Mofebutazone, Oxyphenbutazone, Phenylbutazone, Phenyl Pyrazolidininones, Suxibuzone, Thiazolinobutazone, Salicylic Acid Derivatives such as Bromosaligenin, Fendosal, Glycol Salicylate, Mesalamine, 1-Naphthyl Salicylate, Olsalazine, Sulfasalazine, Thiazinecarboxamides such as Droxicam, Isoxicam, Piroxicam. Others such as epsilon-Acetamidocaproic Acid, S-Adenosylmethionine, 3-Amino-4-hydroxybutyric Acid, Amixetrine, Bendazac, Bucolome, Carbazones, Difenpiramide, Ditazol, Guaiazulene, Heterocylic Aminoalkyl Esters of Mycophenolic Acid and Derivatives, Nabumetone, Nimesulide, Orgotein, Oxaceprol, Oxazole Derivatives, Paranyline, Pifoxime, 2-substituted-4, 6-di-tertiary-butyl-s-hydroxy-1,3-pyrimidines, Proquazone, Sialyl Lewis.sup.x Dimers, or Tenidap. Additional therapeutic agents which can be administered include steroids (e.g., glucocorticoids such as prednisone, methyl prednisolone and dexamethasone).

In addition to administering APC to a subject as described herein, it may be desirable to co-administer an anticoagulant, anti-platelet or thrombolytic agent. Co-administration may include administration prior to APC, simultaneously with APC or following APC administration. Examples of thrombolytic agents include but are not limited to urokinase, tPA, Lys-plasminogen, streptokinase, tissue plasminogen activator, prourokinase, acylated form of plasminogen, acylated form of plasmin, and acylated streptokinase-plasminogen complex or any analogs thereof. Examples of anticoagulants include warfarin and heparin. Further, anticoagulant antibodies, such as those described in U.S. Pat. No. 5,679,639, incorporated by reference, can be co-administered with APC. Anti-platelet agents include, for example, aspirin, dipyridamole, clopidogrel, abciximab (Reopro) or any inhibitor of platelet glycoprotein IIb–IIIa.

Compositions utilized in the present inventions and methods of preparation and administration include those described in U.S. Pat. Nos. 5,084,274, 6,037,322 and 6,156,734, which are herein incorporated by reference each in its entirety. "Activated Protein C" refers to Protein C that is cleaved proteolytically by thrombin to yield an activated protein C (APC) which inactivates coagulation Factors Va and VIIIa thus inhibiting coagulation. The methods of use of APC described herein include fragments of APC, as long as they retain the activities described herein. Such fragments, or APC, include recombinantly produced, human plasma-derived and synthetically produced, for example, as well as derivatives thereof. "Synthetic peptide" refers to a chemically produced chain of amino acid residues linked together by peptide bonds that is free of naturally occurring proteins and fragments thereof. "Anticoagulant" refers to an agent that interrupts coagulation and thereby inhibits fibrin formation. "Coagulation" refers to the sequential process in which the multiple coagulation factors of the blood interact resulting in the formation of fibrin. Protein C consists of a 155 amino acid residue light chain and a 262 amino acid residue heavy chain and is fully described in U.S. Pat. No. 5,679,639 herein incorporated by reference.

"Chemical derivative" refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. APC of the present invention also include any polypeptide having one or more additions and/or deletions or residues relative to the sequence of a polypeptide whose sequence is shown herein, so long as the requisite activity, e.g., anti-inflammatory or neuroprotective, is maintained.

Therapeutic compositions of the present invention contain a physiologically tolerable carrier together with APC, dissolved or dispersed therein as an active ingredient. In a preferred embodiment, the therapeutic composition is not immunogenic when administered to a mammal or human patient for therapeutic purposes.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like.

The preparation of a pharmacological composition that contains active ingredients dissolved or dispersed therein is well understood in the art. Typically such compositions are prepared as injectables either as liquid solutions or suspensions, however, solid forms suitable for solution, or suspensions, in liquid prior to use can also be prepared. The preparation can also be emulsified.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

A therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes.

Liquid compositions can also contain liquid phases in addition to and to the exclusion of water. Exemplary of such additional liquid phases are glycerin, vegetable oils such as cottonseed oil, and water-oil emulsions.

APC is a very species specific moiety. The dosage for human or recombinant human APC in a human is much lower than the appropriate dosage in a mouse, for example. The normal baseline level of APC in a human is typically about 2.2 ng/ml of blood. In practice of the invention methods, it is necessary to administer sufficient APC to raise the blood level slightly above the baseline level, but not so much as to risk causing undesireable bleeding. A therapeutically effective amount of human APC is typically administered to a human at a dosage sufficient to raise the blood level of APC by from about 1.0 ng/ml to about 500 ng/ml, preferably, from about 5 ng/ml to about 200 ng/ml.

The APC can be formulated according to known methods to prepare pharmaceutically useful compositions. The APC is preferably administered parenterally to ensure its delivery into the bloodstream in an effective form by injecting the appropriate dose as continuous infusion for about 4 to about 96 hours. Preferably, the appropriate dose of APC will be administered by continuous infusion for about 4 to about 72 hours. More preferably, the appropriate dose of APC will be administered by continuous infusion for about 4 to about 48 hours. More preferably, the appropriate dose of APC will be administered by continuous infusion for about 12 to about 48 hours. More preferably, the appropriate dose of APC will be administered by continuous infusion for about 12 to about 36 hours. More preferably, the appropriate dose of APC will be administered by continuous infusion for about 4 to about 36 hours. More preferably, the appropriate dose of APC will be administered by continuous infusion for about 12 to about 24 hours. Most preferably, the appropriate dose of APC will be administered by continuous infusion for about 24 hours. The administration of APC will begin as soon as possible following diagnosis of the vascular occlusive or arterial thromboembolic disorder. An appropriate loading dose of APC may be given by bolus injection with or without subsequent APC infusion.

The amount of APC administered can be from about 0.01 mg/kg/hr to about 0.10 mg/kg/hr which is equivalent to about 17 mg/70 kg/24 hours to about 170mg/70 kg/24 hours. While the dose level is identified as a specific amount per 24 hours, one skilled in the art would recognize that this is a designation of the dose level and is not necessarily limited to a 24 hour infusion but may include continuous infusion for various times, for example, from about four hours to about ninety-six hours. More preferably the amount of APC administered is about 0.01 mg/kg/hr to about 0.05 mg/kg/hr (about 17 mg/70 kg/24 hours to about 84 mg/70 kg/24 hours). While more preferably the amount of APC administered will be about 0.01 mg/kg/hr to about 0.03 mg/kg/hr (about 17 mg/70 kg/24 hours to about 50 mg/70 kg/24 hours). Furthermore, the amount of APC administered is from about 0.02 mg/kg/hr to about 0.05 mg/kg/hr which is equivalent to about 34 mg/70 kg/24 hours to about 84 mg/70 kg/24 hours. More preferably the amount of APC administered is about 0.024 mg/kg/hr to about 0.048 mg/kg/hr (about 40 mg/70 kg/24 hours to about 80 mg/70 kg/24 hours). While more preferably the amount of APC administered will be about 0.027 mg/kg/hr to about 0.045 mg/kg/hr (about 45 mg/70 kg/24 hours to about 75 mg/70 kg/24 hours). While more preferably the amount of APC administered will be about 0.030 mg/kg/hr to about 0.042 mg/kg/hr (about 50 mg/70 kg/24 hours to about 70 mg/70 kg/24 hours). While more preferably the amount of APC administered will be about 0.033 mg/kg/hr to about 0.039 mg/kg/hr (about 55 mg/70 kg/24 hours to about 65 mg/70 kg/24 hours). Preferable amounts of APC administered are about 0.024 mg/kg/hr (about 40 mg/70 kg/24 hours), about 0.027 mg/kg/hr (about 45 mg/70 kg/24 hours) or, about 0.030 mg/kg/hr to about 0.042 mg/kg/hr (about 50 mg/70 kg/24 hours). Clearly, the amount of APC can be reduced when administered with a co-factor such as Protein S, as described herein.

Alternatively, the APC will be administered by injecting a portion of the appropriate dose per hour as a bolus injection over a time from about 5 minutes to about 120 minutes, followed by continuous infusion of the appropriate dose for about twenty three hours to about 96 hours which results in the appropriate dose administered over 24 hours to 96 hours.

The most preferable dose level of APC to be administered for thrombotic occlusion (e.g. stroke) as described herein will be about 0.024 mg/kg/hr.

A therapeutically effective amount of an anticoagulant antibody that may be used in conjunction with the methods of the invention is typically an amount of antibody such that when administered in a physiologically tolerable composition is sufficient to achieve a plasma concentration of from about 0.1 microgram (ug) per milliliter (ml) to about 100 ug/ml, preferably from about 1 ug/ml to about 5 ug/ml, and usually about 5 ug/ml.

The therapeutic compositions containing APC are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle. The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgement of the practitioner and are peculiar to each individual. However, suitable dosage ranges for systemic application are disclosed herein and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

The pharmaceutical composition may conveniently be presented in unit dosage form and may be prepared by any of the methods well known in the art of pharmacy. All methods include the step of bringing the compounds into association with a carrier which may contain one or more accessory ingredients. In general, the composition for pills, tablets, or capsules (e.g., for oral administration) or powders are prepared by uniformly and intimately blending the compounds with finely divided solid carriers, and then, if necessary as in the case of tablets, forming the product into the desired shape and size. The pill, tablet, or capsule can be coated with a substance capable of protecting the composition from the gastric acid or intestinal enzymes in the subject's stomach for a period of time sufficient to allow the composition to pass undigested into the subject's small intestine. The pharmaceutical compositions may be also directly targeted to the brain by an intercerebroventricular pump.

Compositions suitable for parenteral administration (e.g., subcutaneous, intravenous, or intermuscular), on the other hand, conveniently comprise sterile aqueous solutions of the compound(s) in water or saline to produce an aqueous solution, and rendering said solution sterile. The composition may be presented in unit or multi-dose containers, for example, sealed ampoules or vials.

In another aspect, the invention provides methods for preventing neuronal death in a patient by administering to a patient a therapeutically effective amount of the pharmaceutical composition of the invention. The pharmaceutical composition of the invention can, for example, be used to treat acute traumatic events such as stroke, CNS trauma (e.g., brain or spinal surgery or injury), injury resulting from neurotoxins, and epilepsy; chronic neurodegenerative diseases such as Huntington's Chorea, Alzheimer's disease, amyotrophic lateral sclerosis (ALS), AIDS-related neuronal degeneration, and brain aging; or other neurodegenerative disorders related to the overactivation of the NMDA receptor.

In particular, it has been discovered that protein S, a co-factor of APC, has a synergistic effect when administered in accordance with the methods of this invention. For example, Example 3 below illustrates that administration of a combination of protein S and APC in the treatment of stroke in a mouse model is more effective for reducing the area of brain infarction and volume of edema in the ischemic hemisphere in mice than is a therapeutically effective low amount of APC administered alone, even when therapy is administered after the ischemic event. This unexpected result is obtained even when the amount of the APC administered (e.g., 0.1 mg/kg) in the combination therapy is far less than is generally used when APC alone is used in treatment of stroke in this model. Thus, a far lower amount of APC is an effective dose when the APC is administered in conjunction with protein S, i.e., simultaneously, before or after administration of the protein S. However, it should be noted that although mice contain endogenous protein S, there is a strong species specificity of APC for the protein S cofactor. It is believed, therefore, that the presence of normal levels of endogenous protein S (e.g.,in humans) substantially lowers (perhaps by a factor of 10-fold to 100-fold) the therapeutic dosage of APC used in the invention methods. Further, it is well known that this synergistic effect of the combined presence of protein S and APC is species specific, depending upon the APC and the cofactor being from the same species. For this reason, when non-human APC is used in treatment of humans or another mammal, it is preferred to co-administer protein S derived from the same non-human species as the APC.

APC, analogs or biologically active fragments thereof may be administered in a manner compatible with the dosage formulation and in such amount as will be therapeutically effective. In particular, it has been discovered that invention treatment methods are equally effective whether the APC is administered during, before or after an ischemic event, such as stroke, suggesting that APC will be effective up to three to six hours after stroke in a human.

The APC-containing compositions of the invention may be administered in any way which is medically acceptable which may depend on the disease condition or injury being treated. Possible administration routes include injections, by parenteral routes such as intravascular, intravenous, intra-arterial, subcutaneous, intramuscular, intratumor, intraperitoneal, intraventricular, intraepidural or others, as well as oral, nasal, ophthalmic, rectal, topical, or by inhalation. The compositions may also be directly applied to tissue surfaces during surgery. Sustained release administration is also specifically included in the invention, by such means as depot injections or erodible implants.

The invention will now be described in greater detail by reference to the following non-limiting examples.

EXAMPLE 1

Animals

Studies were performed in male C57BL/6 mice weighing 23–26 g using procedures approved by the Institutional Animal Care and Use Committee. Mice were subjected to a modified middle cerebral artery (MCA) occlusion technique (E. S. Connolly et al., *Neurosurgery.* 38(3):523–531 (1996); H. Hara et al, *J. Cereb. Blood Flow Metab.* 16:605–611, (1996); and P. Tabrizi et al., *Arterioscler. Thromb. Vasc. Biol.* 19:2801–2806 (1999)) to induce acute focal ischemic stroke with cerebrovascular thrombosis, as described below. Mice were initially anesthetized with metofane and maintained with 50 mg/kg i.p. pentobarbital. Atropine methyl nitrate (0.18 mg/kg i.p.) was given as pre-medication to prevent airway obstruction by mucus formation. Animals were allowed to breath spontaneously. Rectal temperature was maintained at 37±1° C. by a thermostatically regulated heating pad. The right femoral artery was cannulated with a PE-10 catheter for continuous monitoring of blood pressure and blood analysis.

Preparation of Stroke Model

A modified intravascular MCA occlusion technique (Connolly et al., 1996; Hara et al, 1996; and Tabrizi et al., 1999) was used to block the cerebral blood flow (CBF) almost completely in the MCA territory in the ischemic hemisphere. We used non-siliconized uncoated 6–0 8 mm long prolene suture with a modified rounded tip with a diameter of 0.20 mm. With this modification in the tip of the suture, CBF values dropped typically close to 10% of control baseline values immediately after placement of the suture in mice weighing 23–26 g (see below). In contrast, previous studies used nylon filament coated with silicone that does not have thrombogenic properties (Y. R. Wang et al., *Nature Med.* 4:228–231 (1998)) and considered the procedure to be technically successful if ≧50% reduction in relative CBF was observed during the occlusion. The pronounced reduction in the CBF in the present model resulted in significant cerebrovascular thrombosis mainly in small microvessels, large infarcts and stroke-related death often relatively early in the reperfusion phase when CBF was reestablished by withdrawing the suture from cerebral arteries. Briefly, under the operating microscope, the right common carotid artery was exposed through a ventral midline incision, and the external carotid artery and its branches ligated. Through a transverse incision in the artery, the suture was introduced into the external carotid artery lumen, and gently advanced into the internal carotid artery to occlude the MCA at its origin from the circle of Willis. MCA occlusion was maintained for 1 hr followed by 24 hrs of reperfusion.

Blood Flow and Head Temperature Measurements

CBF was monitored by Laser Doppler Flowmetry (LDF) using tissue perfusion monitor (Transonic BLF21, Ithaca, N.Y.). CBF measurements were performed in all animals subjected to neuropathological and neurologic analysis. For CBF determinations, animals were placed in a stereotactic head frame, and readings were obtained 2 mm posterior to the bregma, both 3 and 6 mm to each side of midline, using a stereotactic micromanipulator and keeping the angle of the probe perpendicular to the cortical surface. LDF probes (0.8 mm diameter) positioned on the cortical surface were connected to a tissue perfusion monitor (Transonic BLF21). The procedure was considered to be technically successful if ≧88% reduction in relative CBF was observed immediately after placement of the occluding suture. The procedure was successful in all studied control animals producing levels of ischemia sufficient to render consistently large infarction volumes and microvascular thrombosis in the ischemic hemisphere. Head temperature was monitored with a 36-gauge thermocouple temperature probe in the temporalis muscle connected to a digital thermometer/thermoregulator model (model 9000, Omega, Conn.).

Survival Time and Neurologic Deficits

Survival time was monitored within 24 hrs of reperfusion and stroke-related deaths recorded. Neurologic examinations were performed at 24 hr after reperfusion and in some animals also at 3 hrs of reperfusion. Neurologic findings were scored on the following 5-point modified scale: no neurologic deficit (0); failure to extend left forepaw fully (1); turning to left (2); circling to left (3); unable to walk spontaneously (4); and stroke-related death (5) (Hara et al, 1996 and Tabrizi et al., 1999).

Blood Analysis

Arterial blood gases (pH, $PaO_2$, $PaCO_2$) were measured before and during MCA occlusion using ABL 30 Acid-Base Analyzer (Radiometer, Copenhagen, Denmark).

Measurement of Volume of Injury

The area of injury was delineated by incubation of unfixed 1-mm coronal brain slices in 2% TTC in phosphate buffer (pH 7.4). Serial coronal sections were displayed on a digitizing video screen using the imaging system of Jandel Scientific (San Rafael, Calif.). The volume of injury was calculated by summing up affected areas from each coronal section and multiplying by the thickness of each section. Brain infarction and edema were calculated using Swanson correction (Tabrizi et al., 1999).

Histopathology

Detection of fibrin by immunostaining was performed on brain tissue sections previously treated with TTC. Tissue fixed in 10% buffer formalin was processed and 4 μm thick paraffin coronal sections from each block cut and stained. Fibrin was localized using anti-fibrin II antibody (NYB-T2G1, Accurate Chemical Sci. Corp., Westbury, N.Y.) (1:500 dilution) and graded according to the following scale (P. Tabrizi et al., 1999 and Y. Okada et al., *Stroke.* 25:1847–1853, 1994): 1, fibrin deposition limited to intravascular space; 2, fibrin deposition in the intravascular lumen and the perivascular space; 3, fibrin lattices in the extravascular or parenchymal tissue only. It has been previously shown that anti-human fibrin antibody cross reacts with mouse fibrin (Tabrizi et al., 1999 and H. Weiler-Guettler et al., *J. Clin. Invest.* 101:1983–1991 (1998)). All visual analyses were performed by two observers blinded to the specimen source or timing. Paraffin sections were also stained using the anti-CD11b antibody (DAKO corporation, Carpenteria, Calif.) (1:250 dilution) directed against the leukocyte adhesion receptor macrophage-1 antigen. This antibody detects CD11b antigen on polymorphonuclear leucocytes (PMNs), as well as on activated macrophages and/or microglia in the tissue. The number of CD11b positive cells was counted in ten random fields by two independent blinded observers and expressed as number per $mm^2$ of section. Simultaneous detection of fibrin and leukocytes was done by sequential immunostaining. Fibrin was localized first with the NYB-T2G1 antibody and detected using 3, 3' diaminobenzidine (DAB) substrate (Vector Labs, CA) followed by detection of leukocytes using the CD11b antibody and the Vector SG peroxide substrate (Vector Labs, CA). Routine control sections included deletion of primary antibody, deletion of secondary antibody and the use of an irrelevant primary antibody. Neutrophils were also detected in brain sections by dichloroacetate esterase staining using the esterase staining kit (Sigma, MO) as reported (S. G. Soriano et al, *Stroke.* 30:134–139 (1999)). Sections were deparaffinized and incubated with naphthol AS-D chloroacetate. The free naphthol released on ester hydrolysis by enzymes on neutrophils was detected using freshly formed diazonium salt and counterstained with Gill No.3 hematoxylin. The number of neutrophils was counted as above.

Detection of Fibrin in Brain Tissue Sections by Quantitative Western Blot

The procedure was as discussed previously (Tabrizi et al., 1999 and H. Weiler-Guettler et al., *J. Clin. Invest.* 101: 1983–1991 (1998)). Briefly, after TTC staining, a 1 mm section of brain tissue was divided into contralateral and ipsilateral hemisphere. Tissue was homogenized in 10 mM sodium phosphate buffer, pH 7.5, 0.1 mM aminocaproic acid, 5 mM trisodium EDTA, 10 U aprotinin/ml, 10 U heparin/ml, and 2 mM PMSF. The homogenate was agitated for 14 hour at 4° C., and the particulate material was sedimented by centrifugation at 10,000 g for 10 min, resuspended in extraction buffer without PMSF, sedimented again, and finally dispersed in 3 M urea. The suspension was agitated for 2 hours at 37° C., vigorously vortexed, and centrifuged at 14,000 g for 15 min. The supernatant was aspirated and the sediment dissolved at 65° C. in reducing SDS buffer, subjected to SDS-PAGE (8%), and transferred to a PVDF membrane (Immobilon-P; Millipore Corp., MA) by electroblotting. Fibrin was visualized with anti-human fibrin II antibody (given above) and enhanced chemiluminescence system (Amersham Corp., IL). Fibrin standards were prepared by clotting a known amount of murine fibrinogen (Sigma Chemical Co., MO) with an excess of thrombin in the absence of calcium. The films were scanned with a Hoefer GS 300 scanning densitometer interfaced to an IBM PC computer with a DT 2805 analog and digital system (Data Translation, MA) and data were converted into µg fibrin/0.1 g of tissue.

Spectrophotometric Hemoglobin Assay

This assay was performed to detect microhemorrhages in the brain tissue. The procedure was as described previously (T.F. Choudhri et al., *Stroke.* 28(11):2296–2302 (1997)). Briefly, a section of brain tissue 1 mm thick was divided into ipsilateral and contralateral hemisphere after TTC staining. Distilled water (200 µl) was added, tissue homogenized for 30 sec, sonicated on ice for 1 min, and centrifuged at 13,000 rpm for 30 min. Hemoglobin-containing supernatant was collected, and 80 µl of Drabkin's reagent (Sigma Diagnostics, MO) added to a 20-µl aliquot and allowed to mix for 15 min. This reaction converts hemoglobin to cyanmethemoglobin, which has an absorbency peak at 540 nm. To validate that the measured absorbency reflects the amount of hemoglobin, known quantities of bovine erythrocyte hemoglobin (Sigma) and incremental aliquots of mouse blood added to freshly homogenized brain tissue were analyzed in parallel.

Statistical Analysis

Physiological variables, infarction, and edema volumes were compared between groups using Student's t-test and ANOVA. Non-parametric data (neurologic outcome scores) was subjected to the Chi-square test with Fisher's transformation. Survival was compared by the Kruskal-Wallis test. A value of $p<0.05$ was considered statistically significant.

Results

There were no significant statistical differences in mean arterial blood pressure, $PaO_2$, $PaCO_2$, pH, hematocrit, head and body temperature, and blood glucose between control and APC-treated animals before MCA occlusion, during occlusion, and during reperfusion (data not shown). No changes in head and body temperature were observed due to APC treatment during 15 min pre-MCA occlusion, and all blood parameters during that period were also within normal limits.

No significant differences in baseline tissue perfusion units were observed between control and APC-treated mice, indicating similar pre-occlusion CBF values. Baseline CBF readings were also taken before APC administration, and there was no significant difference with pre-occlusion values, indicating that APC did not influence the CBF under basal conditions. During MCA occlusion, the reductions in CBF in the ischemic hemisphere (point A) were significant in both groups; in the control group, the CBF dropped to between 9–13% of baseline values ($p<0.001$; control MCA group) while in the APC-treated group the CBF was reduced to 13–18% of baseline values (FIG. 1). As shown in Table 1 below, APC treatment resulted in 25% ($p=0.05$) improvement in CBF during occlusion phase relative to control group.

TABLE 1

Effect of APC treatment on CBF during MCA occlusion and reperfusion

| | Pre-occlusion (45–60 min) | | Occlusion (0–60 min) | | Reperfusion (0–60 min) | |
|---|---|---|---|---|---|---|
| | Control n = 7 mice | APC n = 6 mice | Control n = 7 mice | APC n = 6 mice | Control n = 7 mice | APC n = 6 mice |
| Ischemic hemisphere | 100.0 ± 1.2 | 105.0 ± 5.1 | 11.7 ± 3.5 | 14.3 ± 5.9* | 32.3 ± 7.9 | 78.6 ± 22.5** |
| Contralateral hemisphere | 100.0 ± 1.4 | 103.0 ± 5.6 | 91.9 ± 19.3 | 95.7 ± 7.8 | 85.8 ± 17.2 | 93.0 ± 7.9 |

Values are mean ± SD.
The number of CBF measurements during each studied period of time was 6 to 24 for the mean values listed in Table 1. Values are expressed as a percentage of baseline pre-occlusion CBF values determined within 30 min prior to MCA occlusion in either group.
*p = 0.05 and
**p < 0005 for CBF values during occusion and reperfusion respectively.

Figure 1B:
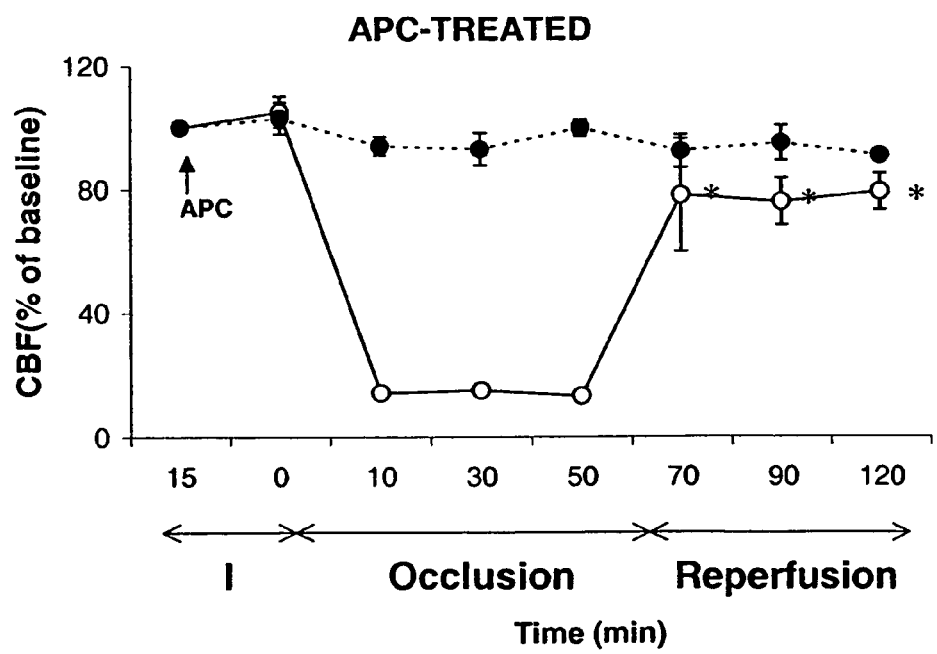

APC, however, did not affect the blood flow in the contralateral non-ischemic hemisphere (point B). During reperfusion, the CBF in the ischemic hemisphere did not exceed 32% of baseline values (FIG. 1A). In contrast, there was a remarkable improvement in CBF during reperfusion in the APC-treated mice, and the values ranged between 71–98% of baseline readings and almost approached control pre-ischemic values (FIG. 1B). The relative increase in CBF during reperfusion in APC-treated animals vs. control was 2.4-fold ($p<0.0005$, Table 1). Again, APC treatment did not affect CBF in non-ischemic hemisphere.

There was a pronounced effect of APC on survival time and neurologic scores after MCA occlusion/reperfusion. As indicated in Table 2 below, a stroke-related death (score 5) with the present technique was observed in 6 out of 7 control animals between 6 and 13 hrs of reperfusion, and only 1 animal survived 24 hrs.

TABLE 2

Survival time and motor neurologic scores at 24 hrs of reperfusion

| | Survival Time | Scores at 24 hrs No. of mice | |
|---|---|---|---|
| Group | (mean ± SD) | 0 1 2 3 4 5 | Score (mean ± SD) |
| Control | 10.2 ± 2.24 | 0 0 0 0 1 6 | 4.86 ± 0.38 |
| APC | 23.7 ± 0.33* | 0 2 2 1 0 1 | 2.33 ± 1.51** |

*p < 0.005 for survival by Kruskal-Wallis test
**p < 0.01 for scores by Chi-square test with Fisher's transformation The mean time of survival in control group was 10.2 hrs. In contrast, 5 out of 6 APC-treated animals survived 24 hrs, and only 1 animal died at 23 hrs. APC-treated animals were sacrificed at 24 hrs to determine the volume of brain injury, and the mean time of survival in APC-treated group was 23.7 hrs. The motor neurological score in APC-treated animals was about 2-fold lower than in control group.

Figure 2A:
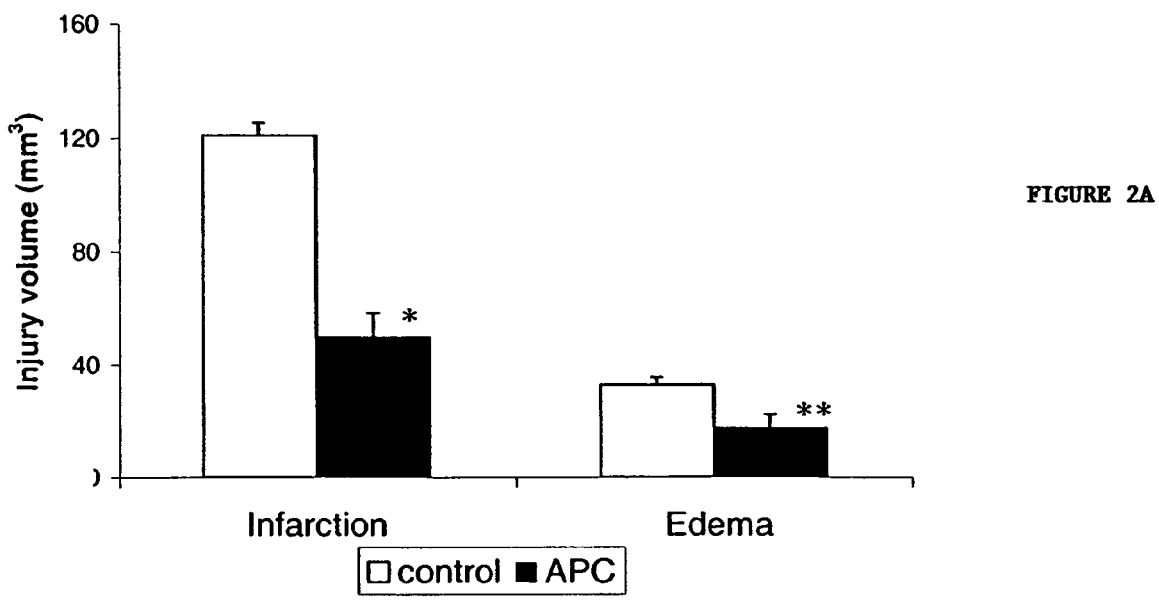
FIGS. 2A and 2B are graphs showing brain injury determined by TTC staining in control and APC-treated mice subjected to 1 hr of transient MCA occlusion.
Figure 2B:
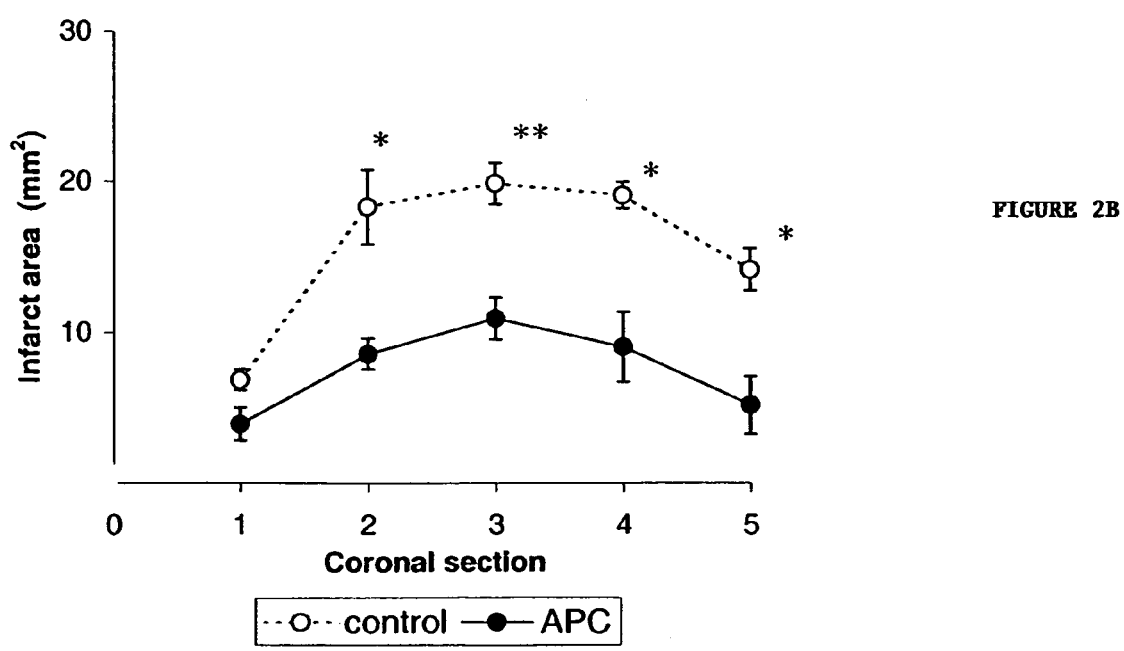
Figure 3A:
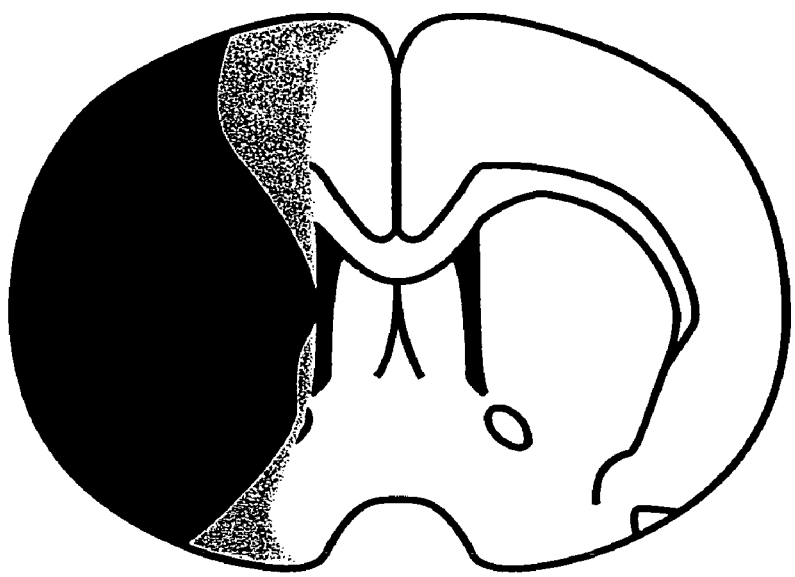
FIGS. 3A and 3B are schematic drawings showing the incidence and topography of the infarction at the level of the optic chasm during transient MCA occlusion in control mice (FIG. 3A) and APC-treated mice (FIG. 3B). The number of control mice and APC-treated mice was 6 and 7 respectively. Key for the incidence of topography (regions involved) is given in FIG. 3A.
Figure 3B:
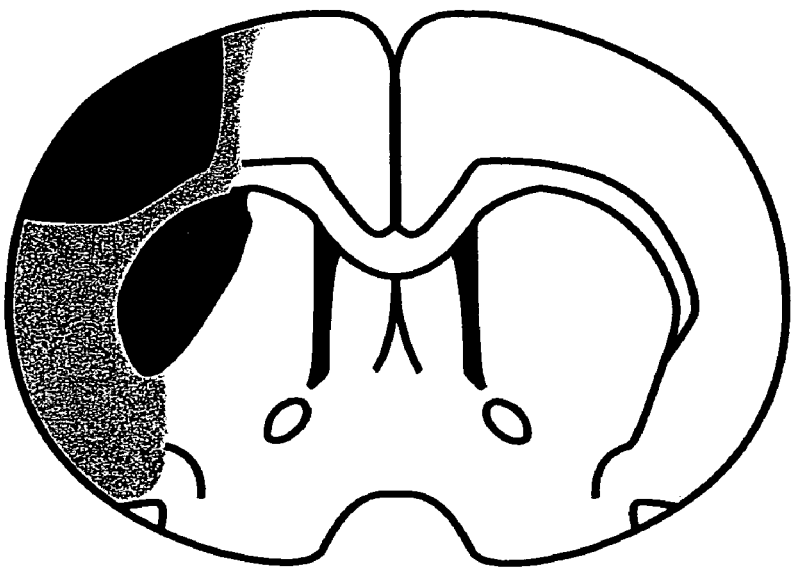

Mice treated with APC had a significant reduction in the volume of brain injury compared to control mice (FIG. 2). The total volume of injury of gray matter (corrected for edema), i.e., the brain infarction volume, was significantly decreased by 59% (p<0.02) in the APC-treated group relative to control mice (FIG. 2A). The edema volume in the lesioned ischemic hemisphere was also reduced by APC treatment by 50% (p<0.05). Studies of the infarct area for each of the five coronal sections of the same brains as in FIG. 2A confirmed significant reductions of injury at all brain levels in APC-treated mice (FIG. 2B). FIG. 3 illustrates that 100% of control mice had injury that involved significant ipsilateral portion of the hemisphere including cortex, subcortical structures and lateral striatum; ≧50% mice exhibited changes in the medial striatum and <50% showed changes in the dorsomedial and ventromedial cortex. In APC-treated animals, there was a significant reduction of the injured area, and all animals developed injury only in small well-localized area in the lateral cortex, with significant reduction of injury in each region.

Immunostaining for Fibrin was Performed After TTC Staining

Several microvessels including small veins, arterioles and numerous capillaries contained intraluminal fibrin deposits corresponding to grade 1 according to the scale of fibrin localization in an MCA model (P. Tabrizi et al., 1999 and Y. Okada et al., 1994). Extravascular deposition of fibrin grade 2 was also found around some microvessels in control mice. The migration of leucocytes into parenchymal tissues was frequently observed in control animals, and PMNs were identified either by morphology or by positive staining for CD11b in the tissue, and/or positive staining for dichloroacetate esterase. In addition to a single antibody staining, sections were also counter-stained with hematoxylin. Double staining for fibrin and leukocytes showed complete thrombosis of a large venule. The expansion of so-called "white thrombus" from the vein into a capillary bed was also shown. The nuclear morphology of neutrophils could not be seen as hematoxylin staining was not performed simultaneously with double staining. Staining with dichloroacetate esterase confirmed infiltration of ischemic parenchymal tissue with PMNs in control mice . It is noteworthy that deposition of fibrin in control mice was much more significant in the present model than in a previous MCA model (Y. Okada et al., Stroke. 25:1847–1853, 1994). The difference could be related to significantly higher reductions in the CBF in the present vs. previous model, both during occlusion, i.e., 88% vs. 63%, and reperfusion, 68% vs. 30%, respectively. Double staining confirmed co-localization of fibrin and leukocytes in cerebral vessels in the ischemic hemisphere in control mice. APC treatment significantly reduced fibrin deposition, as well as vascular accumulation and parenchymal infiltration with PMNs.

Figure 4A:
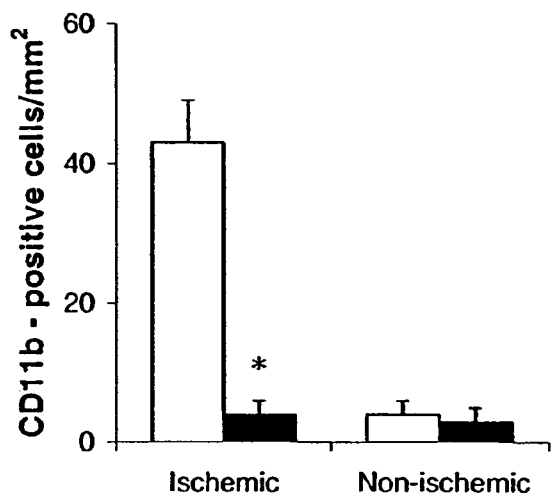
FIGS. 4A through 4D are a series of graphs showing fibrin-positive microvessels (FIGS. 4A and 4C), neutrophils (FIG. 4B) and hemoglobin levels (FIG. 4D) in the ischemic and contralateral hemisphere in control mice and APC-treated mice determined after 1 hr of transient MCA occlusion. Fibrin positive vessels and leukocytes were detected by immunostaining with anti-fibrin II antibody and CD11b antibody and dichloroacetate staining respectively. Hemoglobin levels in hemispheric sections were determined by spectrophotometric hemoglobin assay. Values are mean±SE. n=6 for control mice (open bars) and n=7 for APC-treated mice (closed bars).
Figure 4B:
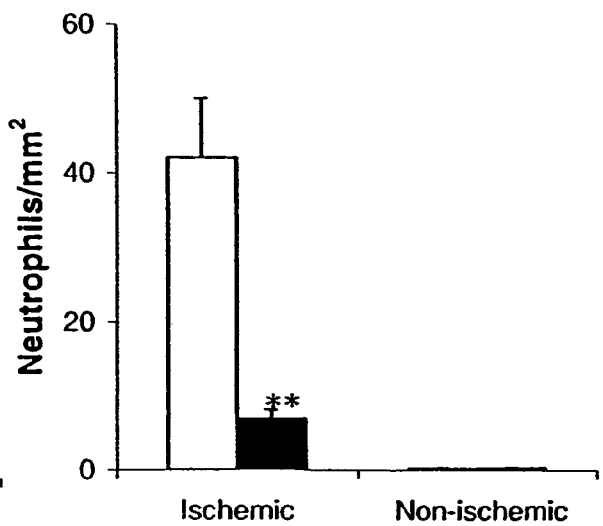
Figure 4C:
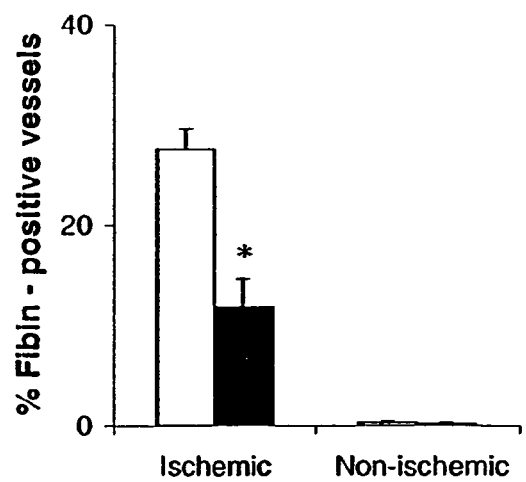
Figure 4D:
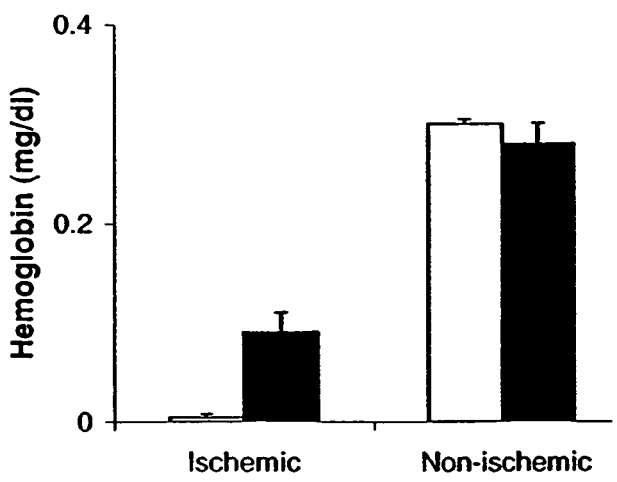

The number of fibrin-positive microvessels in the ischemic hemisphere in the area of infarction was reduced by about 2.5-fold in APC-treated animals compared to control mice (FIG. 4A). However, it is important to note that fibrin staining was much weaker on simultaneously stained tissue sections in APC-treated animals than in control mice, so that the number of fibrin positive vessels does not reflect accurately the amount of fibrin deposited in tissue, as indicated by the more sensitive quantitative Western blot analysis (FIG. 5). The number of CD11-b positive cells in tissue and the number of dichloroacetate esterase positive neutrophils was the same in control mice suggesting that most (if not all) of CD11b positive cells could in fact be PMNs (FIG. 4B). The number of PMNs in tissue dropped by 11.2-fold in APC-treated animals (FIG. 4B). Macroscopic inspection and histologic analysis indicated no intracerebral bleeding or subarachnoid hemorrhage in APC-treated animals. These results were corroborated by barely detectable hemoglobin levels in the ischemic hemisphere both in APC-treated animals and in control animals that were even below the values in the contralateral non-ischemic hemisphere (FIG. 4C) confirming the absence of microbleeding in ischemic brain tissue. Hemoglobin values were particularly low in the ischemic hemisphere in control animals possibly reflecting minimal vascular entrapment of red blood cells due to brain swelling and impaired re-circulation.

Figure 5A:
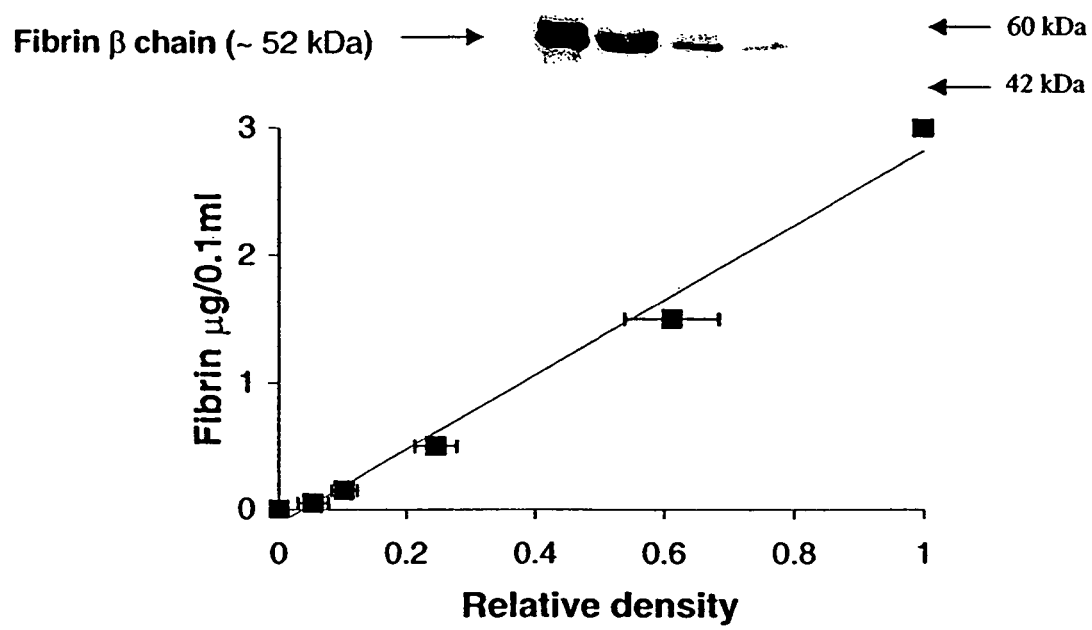
FIGS. 5A and 5B are graphs showing Western blot detection of fibrin in brain sections of control and APC-treated mice with anti-fibrin NYB-T2G1 antibody.
Figure 5B:
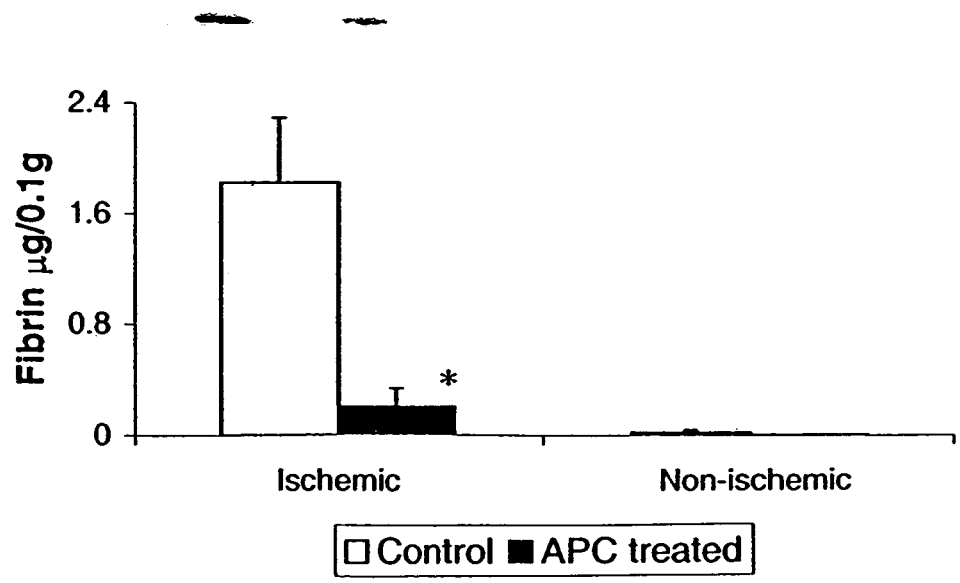

FIGS. 5A and 5B illustrate 8.2-fold decrease in the amount of deposited fibrin in ischemic hemisphere of APC-treated vs. control mice determined by quantitative Western blot analysis.

EXAMPLE 2

Figure 6D:
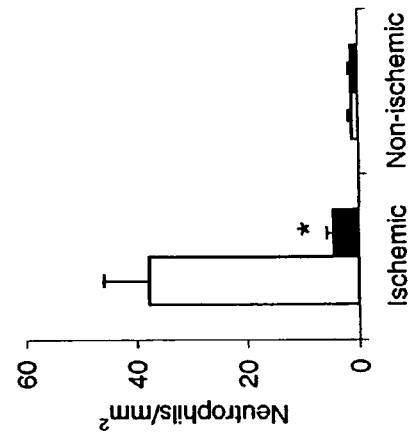
FIGS. 6A through 6E are graphs showing brain infarction area (FIG. 6A) and edema volume (FIG. 6B), cerebral blood flow (CBF) during reperfusion (FIG. 6C), neutrophils (FIG. 6D) and fibrin-positive vessels (FIG. 6E) in ischemic hemisphere in mice treated with vehicle or APC after stroke induction. Vehicle (open bars), or APC (2 mg/kg, closed bars), 0.5 mg/kg (light gray bars) and 0.1 mg/kg (dark gray bars) were given 10 min after the MCA occlusion. Mean±SE, from 3 to 5 animals. *p<0.05 and **p<0.01.
Figure 6E:
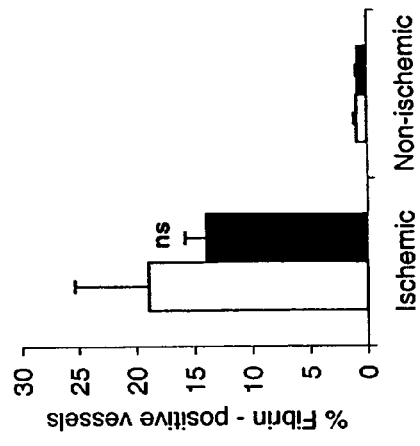
Figure 6A:
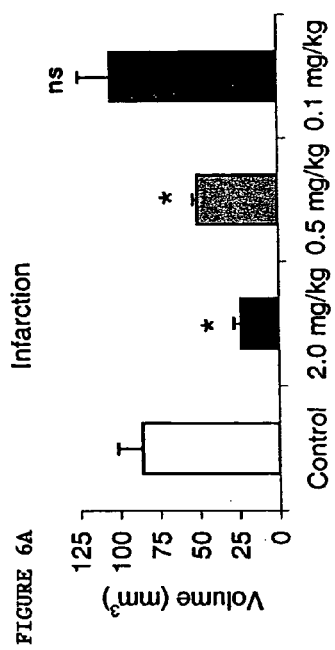
Figure 6B:
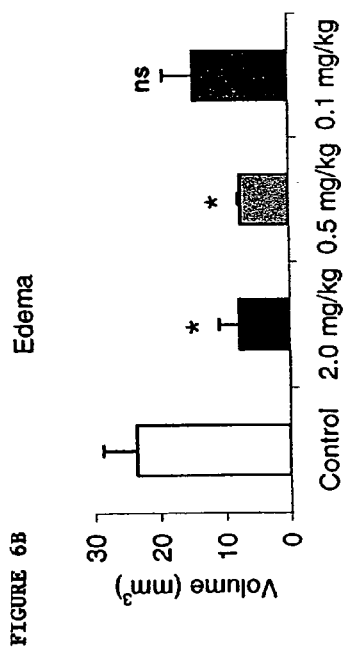
Figure 6C:
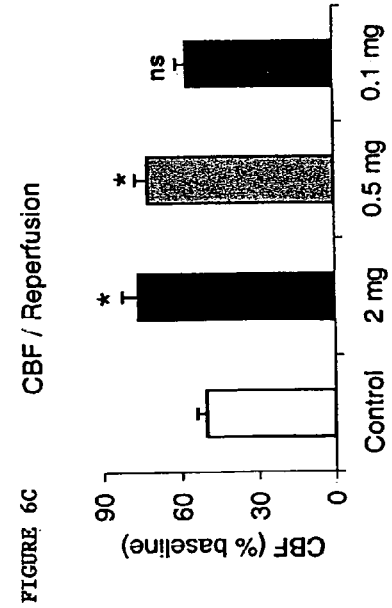

The effects of administration of APC post occlusion was studied in a separate set of experiments using the methods and materials described above in Example 1 above, except that APC (2 mg/kg) was administered to mice 10 min after the MCA occlusion. infarction volume was reduced by 69% (p<0.03) (FIG. 6A) and edema volume was reduced by 61% (p<0.05) (FIG. 6B), cerebral blood flow was restored towards control values (FIG. 6C), and brain accumulation of neutrophils was eliminated (FIG. 6D). In addition, the decrease in the number of fibrin positive vessels in the ischemic hemisphere was 25%, an insignificant amount in comparison to vehicle-treated controls (FIG. 6E). Thus, APC reduced volumes of brain infarction and edema in a dose-dependent fashion (FIGS. 6A and B) and produced a dose-dependent restoration in CBF during reperfusion (FIG. 6C).

Figure 7:
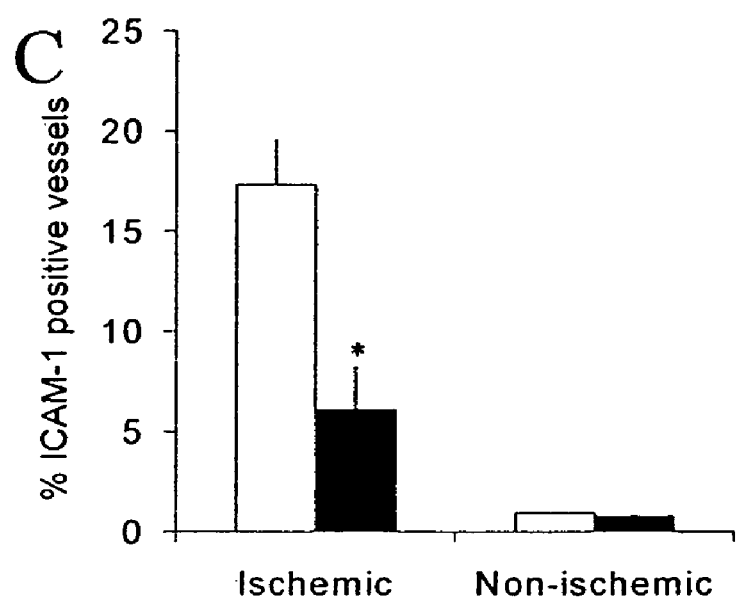
FIG. 7 is a graph showing the percentage of ICAM-1-positive vessels (mean±SE) in control (n=4; open bars) and APC-treated mice (n=4; closed bars) after treatment with 2 mg/kg APC given 10 min after the MCA occlusion.

In this post-occlusion administration model, immunostaining for ICAM-1 in the ischemic hemisphere indicated that APC administration after the onset of ischemia reduced the intensity of ICAM-1-positive blood vessels, and the number of ICAM-1-positive blood vessels was reduced by 61% (FIG. 7).

Table 3 below shows the cumulative results of experiments conducted with mice treated with APC (2 mg/kg) 15 min prior to or 10 min after the MCA occlusion had no significant differences in mean arterial blood pressure, $PaO_2$, $PaCO_2$, pH, hematocrit, head temperature, and blood glucose when compared with control animals (data not shown). APC administration did not influence CBF under basal conditions in the absence of occlusion/reperfusion.

TABLE 3

Survival and motor scores at 24 hrs post MCA occlusion/reperfusion

| | | Scores at 24 hours post MCAO | |
|---|---|---|---|
| Group Control | Survival Time (hr) (mean ± SD) | No. of mice 0 1 2 3 4 5 | Mean Score (± SD) |
| APC 15 min prior to MCAO | 13.6 ± 3.24 | 0 0 0 2 2 8 | 4.50 ± 0.79 |
| 2 mg/kg | 23.7 ± 0.33* | 0 2 2 1 0 1 | 2.33 ± 1.51** |
| APC 10 min after MCAO | | | |
| 2 mg/kg | 24.0 ± 0.00* | 1 3 1 0 0 0 | 1.25 ± 0.96* |
| 0.5 mg/kg | 24.0 ± 0.00* | 0 1 1 1 0 0 | 2.00 ± 1.00* |
| 0.1 mg/kg | 14.3 ± 6.43[ns] | 0 0 0 1 0 2 | 4.33 ± 1.15[ns] |

APC or vehicle was administered 15 mm prior to or 10 after stroke induction. The difference between control animals treated with vehicle prior to or after MCA occlusion (MCAO) was not significant and data for controls were pooled.
*$p < 0.005$ for survival by Kruskal-Wallis test for APC-treated vs. control group; *$p < 0.005$;
**$p < 0.01$ for scores by Chi-squared test with Fisher's transformation test for APC-treated vs. control group;
[ns]non-significant.

The mean survival time for control group animals was 13.6 hours. Ten of 11 mice treated with 2 mg/kg APC either 15 min prior to occlusion or 10 min after occlusion survived 24 hrs, and 1 APC-treated animal died at 23 hours. All 3 animals treated with 0.5 mg/kg APC at 10 min after stroke induction survived 24 hours. APC-treated animals were sacrificed at 24 hrs to determine the volume of brain injury, thus data beyond 24 hours is not available.

The motor neurological scores in mice given 2 mg/kg APC 15 min prior to and 10 min after the MCA occlusion were improved by 2 to 2.7-fold compared with control group. Also, 0.5 mg/kg APC given 10 min after MCA occlusion improved neurological outcome significantly. However, the protective effect of APC was not apparent at an APC dose of 0.1 mg/kg based on survival time and neurologic function (Table 1) and on the volume of brain injury and effects on CBF (FIG. 7).

EXAMPLE 3

Figure 8A:
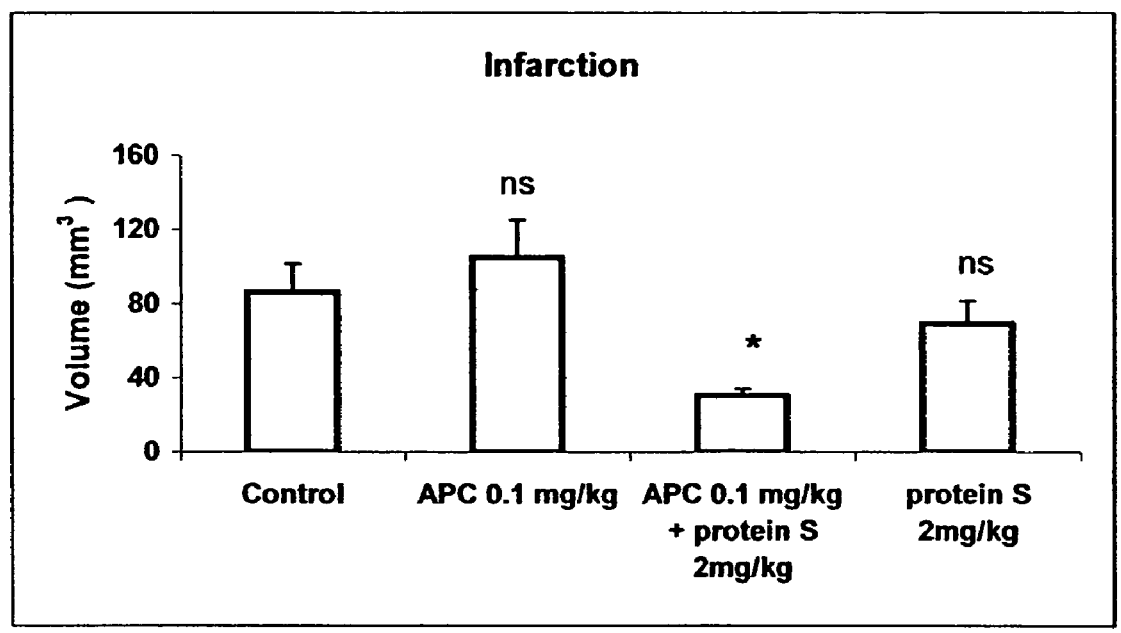
FIGS. 8A and 8B are graphs showing infarction area (FIG. 8A) and edema volume (FIG. 8B) in the ischemic hemisphere in mice after stroke induction treated with vehicle alone (control), low dose (0.1 mg/kg) of APC alone, low dose APC coinjected with protein S (2 mg/kg) or protein S alone. Mean±SE, from 2 to 5 animals. *p<0.05 and ns=non-significant.
Figure 8B:
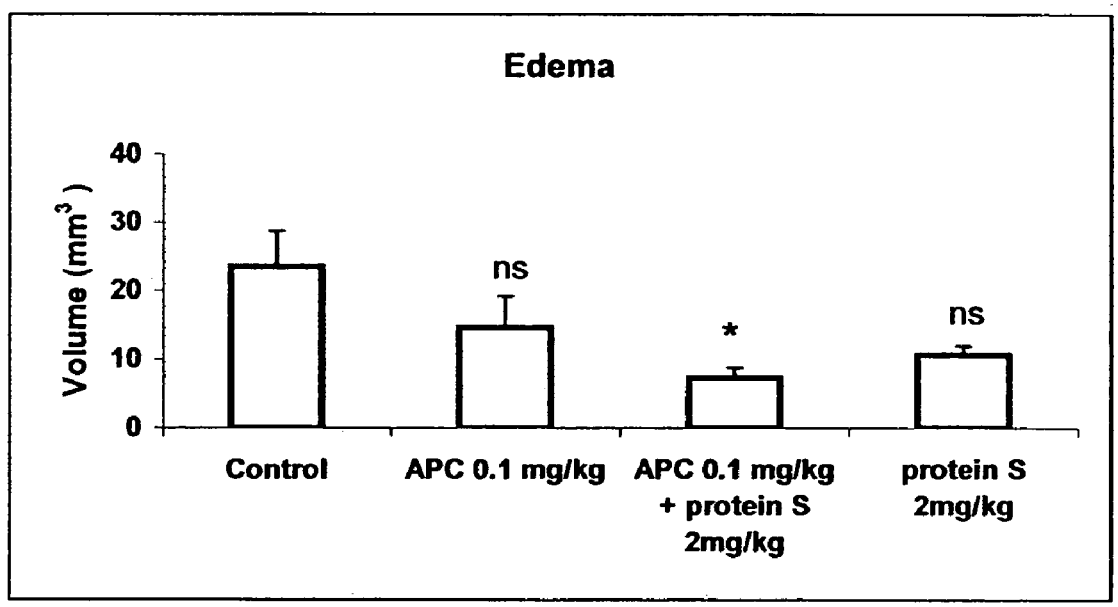

The effects of administration of protein S, a non-enzymatic cofactor of APC, was studied in a separate set of experiments using the methods and materials described above in Example 1. Either vehicle, protein S (2 mg/kg) alone or protein S (2 mg/kg) co-injected with a low dose of APC (0.1 mg/kg) was injected 10 minutes after the MCA occlusion. The results shown in FIGS. 8A and 8B indicate that the low dose of APC alone was not protective. However, co-injection of protein S (2 mg/kg) and APC (0.1 mg/kg) produced a synergistic effect, significantly reducing brain infarction and edema by 71% ($p<0.008$) and 51% ($p<0.05$), respectively, in the focal brain ischemia model.

While the invention has been described in detail with reference to certain preferred embodiments thereof, it will be understood that modifications and variations are within the spirit and scope of that which is described and claimed.

What is claimed is:

1. A method of protecting neuronal cells from cell death in a subject having or at risk of having a stroke, comprising administering to the subject, a therapeutically effective amount of activated protein C (APC) in a bolus injection and a therapeutically effective amount of protein S, wherein said therapeutically effective amount of protein S comprises about 2 mg/kg, thereby providing neuroprotection to the subject.

2. A method for reducing neurological inflammation in a subject having or at risk of having a stroke, comprising administering to the subject, a therapeutically effective amount of activated protein C (APC) in a bolus injection and a therapeutically effective amount of Protein S, wherein the APC is administered during the stroke, or up to six hours before or after the stroke, and wherein said therapeutically effective amount of protein S comprises about 2 mg/kg, thereby reducing neurological inflammation in the subject.

3. A method for reducing neurological inflammation in a subject having or at risk of having inflammatory vascular disease comprising administering to the subject, a therapeutically effective amount of activated protein C (APC) in a bolus injection and a therapeutically effective amount of Protein S, wherein said therapeutically effective amount of protein S comprises about 2 mg/kg, thereby reducing neurological inflammation in the subject.

4. The method of any of claims 1, 2 or 3 further comprising administering a continuous infusion of APC following the bolus injection.

5. The method of claim 1, wherein the APC is administered intravenously.

6. The method of claim 1, wherein the APC is administered during the stroke or up to six hours before or after the stroke.

7. The method of claim 2, wherein the APC is administered intravenously.

* * * * *